United States Patent [19]
Horky et al.

[11] Patent Number: 6,156,765
[45] Date of Patent: Dec. 5, 2000

[54] METHOD OF TREATING AND PREVENTING VASOSPASM

[75] Inventors: Laura L. Horky, Nashville, Tenn.; Robert J. Boock, Olney, Md.

[73] Assignee: The United States of America as represented by the Department of Health and Human Services, Washington, D.C.

[21] Appl. No.: 08/672,060

[22] Filed: Jun. 26, 1996

[51] Int. Cl.[7] .............................. A61K 31/44; C12N 1/20; B65D 81/24

[52] U.S. Cl. ......................... 514/292; 514/340; 435/810; 206/570

[58] Field of Search ..................................... 514/340, 292; 206/570; 435/810

[56] References Cited

PUBLICATIONS

Ohmoto, T., et al, Neurol. Med–Chir., 1979, 19(1), pp. 73–82, abstract only.
Oubidar, M., et al, Free Radical Biology and Medicine, vol. 16(6), pp. 861–867, abstract only, Jun. 1994.
Macdonald, R.L., et al, Stroke, vol. 22(8), pp. 971–982, Aug. 1991.
Cecil Textbook of Medicine, edited by J. Wyngaarden et al, W.B. Saunders Co., pp. 2163–2165, Oct. 1992.
Morooka, Acta Med Okayama, vol. 32(1), pp. 39–49, 1973.
Ikeda, Neurosurgery, vol. 24(6), pp. 820–824, 1989.
River, Y. et al, Movement Disorders, 1994, 9(5), pp. 559–562.
Oubidar, M. et al, Free Radical Biology & Medicine, 1994, 16(6), pp. 861–867.
Comparative Study of Different Iron–Chelating Agents in Cold, Induced Brain Edema, Y. Ikeda et al., Neurosurgery, vol. 24, No. 6, 1989, pp. 820–824.
Cerebral Arterial Spasm. II Etiology and Treatment of Experimental Cerebral Vasospasm, H. Morooka, Acta Med. Okayama, vol. 32, No. 1, 1978, pp. 39–49.
Chemical Abstracts 124:106078, Vollrath, 1995.
Chemical Abstracts 118:57455, Harada, 1992.
Chemical Abstracts 113:95352, Simon, 19910, 1990.

*Primary Examiner*—D. Margaret Seaman
*Attorney, Agent, or Firm*—Fitch, Even, Tabin & Flannery

[57] ABSTRACT

The present invention is drawn to a method of preventing or treating vasospasm by administering to a patient an effective amount of an iron chelator which preferentially chelates ferrous iron over ferric iron. The iron chelators to be use in the present invention are small compounds which can penetrate the blood-brain barrier and act intracellularly to chelate ferrous iron. The present invention further encompasses a kit to be used for the prevention and treatment of vasospasm with the method of the invention.

16 Claims, 1 Drawing Sheet ively small in size and hydrophobic will typically possess good CNS penetration (so that they can cross the blood-brain barrier) as well as act intracellularly.

METHOD OF TREATING AND PREVENTING VASOSPASM

BACKGROUND OF THE INVENTION

Subarachnoid hemorrhage may be caused by trauma or by non-traumatic incidents, such as a ruptured intracranial aneurysm, arteriovenous malformation, or vasculitis. Cerebral arterial vasospasm is the leading cause of morbidity and mortality in patients surviving subarachnoid hemorrhage (SAH). Oxyhemoglobin appears to be responsible for vasospasm after SAH. Much existing evidence suggests that oxyhemoglobin is the clinically-relevant vasospastic agent. The presence of high concentrations of extracellular oxyhemoglobin in the cerebrospinal fluid (CFS) correlates with the presence of spasm in primates [Macdonald et al., Stroke 22:971–982 (1991)].

Concentrations of extracellular oxyhemoglobin are highest on post-SAH days 4 to 7, which corresponds with the onset of vasospasm. Oxyhemoglobin is no longer detectable in the CSF 14 to 21 days after SAH, which corresponds with resolution of vasospasm. Furthermore, intact erythrocytes are inert, whereas lysed erythrocytes are vasospastic, in vitro and in vivo. Lastly, oxyhemoglobin is vasospastic, whereas the oxidized methemoglobin is not.

The results of some experiments suggest that the iron in oxyhemoglobin causes vasospasm by generating free radicals and lipid peroxides.

Iron catalyzes the production of free radicals, which can cause damage to vascular smooth muscle, endothelial cells, and perivascular nerve endings, each an active participant in the normal vasoregulatory response [Macdonald et al., Stroke 22:971–982 (1991)]. Investigators have previously examined the therapeutic potential of iron chelators, oxidizing agents, and free radical scavengers, but with limited success.

Studies with ferric iron chelators such as deferoxamine in potential therapies for vasospasm have had only limited success [Harada et al., J. Neurosurg. 77:763–767 (1992)], [Vollmer et al., Neurosurgery 28:27–32 (1991)]. Deferoxamine has many shortcomings as a potential preventive therapy for delayed vasospasm. Deferoxamine has only limited penetrability of the blood-brain barrier, and adequate CSF levels cannot be achieved before toxic systemic effects appear [Peters et al., Biochem. Pharmacol. 15:93–109 (1966)], [Oubidar et al., Free Radical Biology and Medicine 16:861–867 (1994)]. Deferoxamine acts mainly extracellularly and chelates only free iron, and not heme or ferritin-bound iron. Furthermore, deferoxamine has a much greater affinity for ferric iron ($Fe^{+3}$) than for ferrous iron ($Fe^{+2}$) (the deferoxamine-iron stability constants are $10^{31}$ for $Fe^{+3}$ and $10^2$ to $10^{14}$ for $Fe^{+2}$). Therefore, deferoxamine acts only extracellularly and on unbound iron, and it does not chelate the ferrous state of iron responsible for free radical damage and possibly also responsible for the "sink effect."

Others propose that vasospasm results from a regional disruption in the balance of both constrictive and dilatory vascular regulation.

Oxyhemoglobin may induce damage by binding to nitric oxide (NO) molecules and locally limiting the availability of NO for vasodilation, in the so-called "sink effect" [Moncada et al., NeuroReport 3:530–532 (1992)].

Vasodilation is normally maintained by NO [Moncada et al., NeuroReport 3:530–532 (1992)]. Hemoglobin has a strong affinity for NO, binding to NO 1,500-fold more readily than to oxygen. NO normally binds to a ferrous heme moiety in the enzyme guanyl cyclase (which catalyzes the conversion of GTP to cyclic GMP in smooth muscle cells, and thereby decreases intracellular free calcium levels, causing vascular smooth muscle cells to relax). Since NO binds to the ferrous heme moiety of guanyl cyclase, it is possible that excess quantities of extracellular $Fe^{+2}$, whether free or bound to heme in the perivascular space, may exert a powerful sink effect, limiting the availability of NO. This possibility is supported by the reversal of vasospasm by the intracarotid infusion of NO [Afshar et al., J. Neurosurg. 83:118–122 (1995)] from a short-lived donor of NO.

SUMMARY OF THE INVENTION

One object of the present invention is to provide an improved method or kit for preventing or treating vasospasm. This is accomplished by administering to a patient an effective amount of an iron chelator which preferentially chelates ferrous iron.

DETAILED DESCRIPTION OF THE INVENTION

Figure 1:
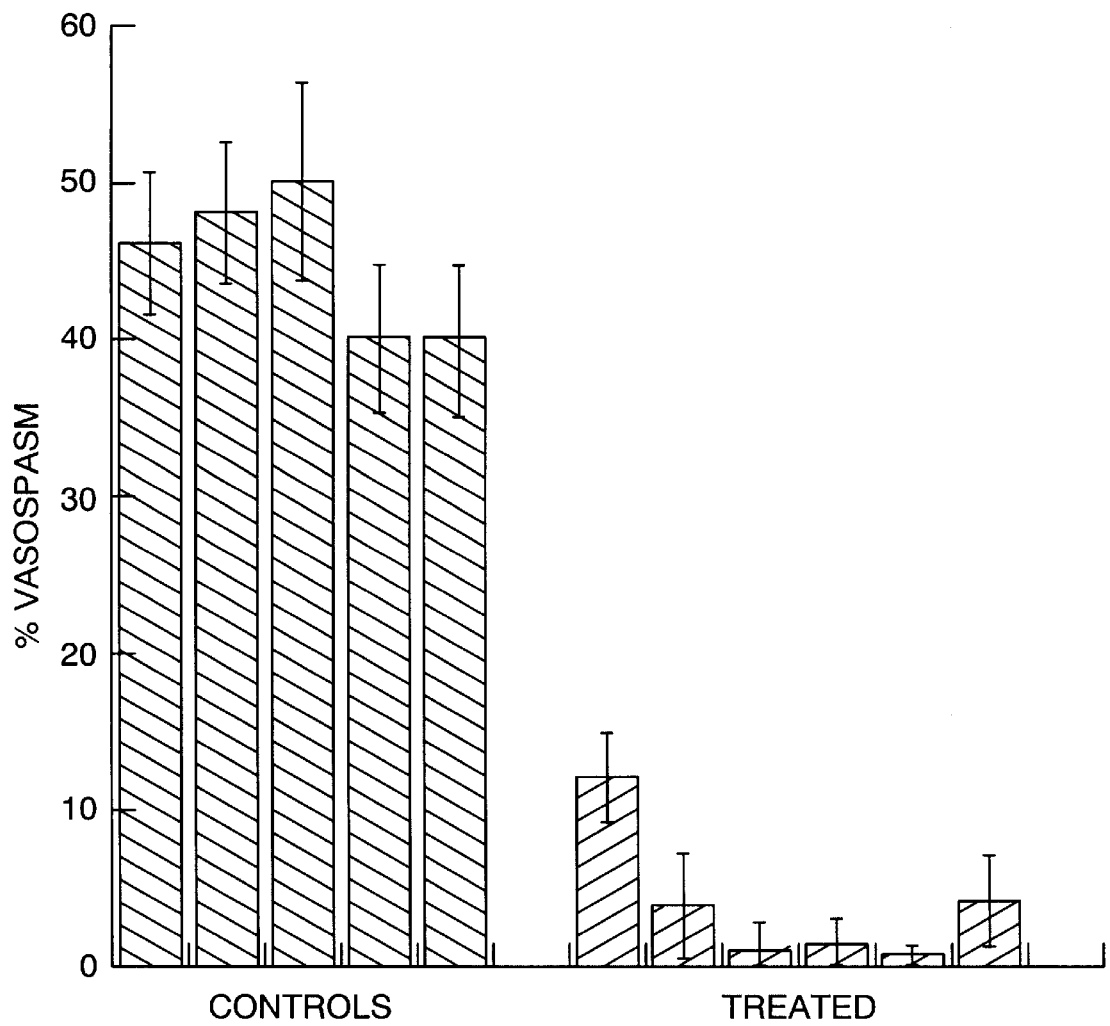
FIG. 1 shows the effect of ferrous iron chelators in prevent vasospasm.

The present inventors have determined that ferrous iron from oxyhemoglobin is connected to the vasospastic response which occurs after subarachnoid hemorrhage. The present invention is a method of preventing the vasospasm with the use of iron chelators. Iron chelators used in the method of the present invention should be those which preferentially chelate the ferrous form of iron, as compared to ferric iron.

Because of the desire to use the present method to prevent vasospasm following subarachnoid hemorrhage, in addition to the preferential chelation of ferrous iron, chelators to be used in the present invention should also be able to penetrate the blood-brain barrier in an amount effective to prevent or reduce the extent or likelihood of vasospasm following subarachnoid hemorrhage, as well as treat vasospasm if it has occurred. Further, iron chelators to be used in the method of the present invention should be able to act intracellularly, thus chelating the ferrous iron before it is released to the extracellular space. Compounds which are relatively small in size and hydrophobic will typically possess good CNS penetration (so that they can cross the blood-brain barrier) as well as act intracellularly.

Compounds which preferentially chelate ferrous iron, possess good CNS penetration and act intracellularly include, but are not limited to 2,2'-dipyridyl and 1,10-phenanthroline.

In addition to chelating ferrous iron, the present compounds may optionally have the added mechanism in preventing vasospasm by inducing heme oxygenase. Heme oxygenase is an enzyme which is naturally induced in vivo in response to heme-associated endothelial damage. Heme oxygenase catalyzes the degradation of heme to iron, biliverdin (a natural antioxidant) and carbon monoxide. The induction of heme oxygenase in the CNS by the compounds of the present invention may contribute to their ability to prevent or treat vasospasm.

Using the method of the present invention ferrous iron chelators are administered to a patient (human or other mammal) to prevent or treat vasospasm.

Because of the ability of the compounds used in the present invention to penetrate the blood brain barrier and their small size they may be administered either intravenously or orally.

In addition, if for therapeutic administration, the ferrous iron chelators may be included in a composition containing 0.1%–99%, preferably 1%–90%, more preferably 10%–80% by weight of the chelator with a suitable pharmaceutically acceptable carrier. Such pharmaceutical carriers include materials useful for the purpose of administering the medicament, which are preferably non-toxic, and may be solid, liquid or gaseous materials, which are otherwise inert and medically acceptable and are compatible with the active ingredients.

If administered orally, the ferrous iron chelators may be in the form of fine powders or granules and may contain diluting, dispersing and/or surface active agents, and may be presented in a draught, in water or in a syrup; in capsules or sacnets in the dry state or in a non-aqueous solution or suspension, wherein binders and lubricants may be included; or in a suspension in water or a syrup. Where desirable or necessary, flavoring, preserving, suspending, thickening or emulsifying agents may be included. Tablets and granules are preferred, and these may be coated. When administered orally, the dosage may be administered every four hours or on a suitable time regime to allow continuous action of the drugs in the body.

If administered intravenously, the compounds may be administered either continuously over a prolonged period of time or as one or more bolus injections. If administered continuously, the compounds may be present in any pharmaceutically acceptable buffered saline carrier solution and may be administered prior to the onset of a condition which induces vasospasm up to ten to fourteen days after the occurrence of said condition. For example, in the event of an aneurysm, the compounds may be administered continuously from the onset of the subarachnoid hemorrhage up to ten to fourteen days after its repair.

It is also anticipated that, due to the rapid action of the compounds, the present method may be applicable to the treatment of vasospasm, particularly when administered intravenously in a high dose bolus form.

The amount of ferrous iron chelator to be administered to a patient must be sufficient to effectively chelate ferrous iron and prevent or reduce vasospasm but not result in toxicity from the compound. Typically the ferrous iron chelators may be administered in a dose range of 20–100 mg/kg/day. An effective amount of the compounds will be one which reduces the vasospasm by at least $\geq 10\%$. Preferably vasospasm will be reduced by $\geq 20\%$; more preferably by $\geq 50\%$ and most preferably by >95%.

To prevent vasospasm, ferrous iron chelators are administered up to 3–4 days after the initial bleed, preferentially 1–2 days after the initial bleed, most preferably as rapidly as possible after the initial bleed and may be administered continuously to delay surgery, thus providing for improved surgery results and clinical stabilization of the patients.

The present invention also encompasses a kit to be used with the method of the present invention. The kit may contain a vial which contains the ferrous chelator and suitable carriers, either dried or liquid form. The kit further comprises instructions in the form of a label on the vial and/or in the form of an insert included in a box in which the vial is packaged, for the use and administration of the compounds. The instructions may also be printed on the box in which the vial is packaged. The instructions contain information such as sufficient dosage and administration information so as to allow a worker in the field to administer the drug. It is anticipated that a worker in the field encompasses any doctor, nurse, or technician who might administer the drug, as well as any emergency medical or trauma personnel who might administer the drug under emergency response situations.

The following experiments demonstrate the effective prevention of vasospasm in an acceptable primate model using the exemplified iron chelator 2,2'-dipyridyl. The primate model used is considered to be the best in the field to study vasospastic responses and is considered by those skilled in the art to be correlative with humans. It should be noted that the present invention is not limited to the specific use of the exemplified iron chelator, as it is expected that any iron chelator which preferentially chelates ferrous iron, can penetrate the blood brain barrier and act intracellularly will be effective in the present invention.

EXAMPLES

Methods and Materials

Eleven (11) cynomologous macaques (8 male and 3 female, weight 3.0–5.9 kg.) were randomly divided into 2 groups. Craniotomy was performed in all animals and autologous clot was placed around the right middle cerebral artery (R MCA) after the arachnoid membrane was removed, as described elsewhere [Pluta et al., J. Neurosurg. 77:740–748 (1992)]. Six animals (3 male and 3 female) received IV infusion of 2,2'-dipyridyl (70 mg/kg/day) continuously for 14 days. Between postoperative days 7 and 10, cerebral arteriography was used to assess the presence and degree of vasospasm using methods previously described [Pluta et al., J. Neurosurg. 77:740–748 (1992)]. The five control animals (all male) received IV infusion of saline in a volume equal to that delivered in the experimental group (10–15 cc/kg/day). Two pilot animals were also used in an initial phase in order to establish an effective experimental dose. One received 44 mg/kg/day of IV 2,2'-dipyridyl, and the other received up to 100 mg/kg/8 hrs of IV 2,2'-dipyridyl.

Preparation of 2,2'Dipyridyl 2,2'-dipyridyl (Sigma, St. Louis, Mo.), M. Wt. 156.2, ($C_{10}H_8N_2$), was dissolved in sterile 0.45% normal saline at 6 mg dipyridyl/cc saline. The mixture was sterilized by filtration and protected from UV light.

Arteriography

Each monkey underwent arteriographic study of the R MCA 3 to 21 days before surgery and 7 to 10 days after clot placement [Pluta et al., J. Neurosurg. 77:740–748 (1992)]. Under general anesthesia (ketamine 10 mg/kg and isoflurane) and sterile conditions, a cutdown of the right femoral artery was performed and a No. 3 French catheter was advanced to the right ICA. Fluoroscopy (C-arm; OEC) and intravenous contrast (2 cc Conray, 60%; Malinkrodt Medical, St. Louis, Mo.), were used to acquire subtraction images of the vessel. A radiopaque ruler was placed in the field to allow standardized measurements.

All studies were performed in the standard anteroposterior projection (AP). During the arteriography, the end-tidal $CO_2$ was maintained at 40 mm Hg and core body temperature was maintained at 37 degrees Celsius using a heating pad. Blood pressures were monitored during all procedures.

Placement of Subarachnoid Clot and Indwelling Intravenous Catheter

As in previous studies [Pluta et al., J. Neurosurg. 77:740–748 (1992)], each animal was anesthetized as follows. Each monkey was given an injection of ketamine (10 mg/kg IM), atropine sulfate (0.05 mg/kg IM), and sodium thiopental (25 mg/kg IV). The animals were intubated and ventilated with isoflurane (0.5%–1.0%) and 100% $O_2$ and paralyzed with pancuronium (0.1 mg/kg). Each animal was hyperventilated to an end-tidal $CO_2$ of 30 to 40 mm Hg.

Each animal was placed in the supine position for a right frontotemporal craniotomy. Under sterile conditions, the dura was opened and the R MCA was identified in the sylvian fissure. Using the operating microscope, the arachnoid membrane over the R MCA was dissected from the trifurcation to the origin of the vessel at the ICA bifurcation. 8–10 cc of autologous clotted arterial blood obtained by an assistant via a left femoral cutdown was then placed along the length of the exposed vessel. The dura was then closed in a watertight fashion, followed by the muscle and skin layers.

Each animal was then repositioned for placement of a 6.6 French Broviac catheter in the left femoral vein. The tip of the catheter was guided to the inferior vena cava, and the catheter was secured at the level of the femoral vein. The distal end of the catheter was passed subcutaneously to the midscapular region and secured. Each monkey was fitted in a jacket containing an infusion pump (Disetronic Medical Systems, Plymouth, Minn.) which delivered 70 mg/kg (60 cc/24 hours) of the 2,2'-dipyridyl solution. Each monkey was sedated daily with ketamine (10 mg/kg IM) to change the delivery pump. The Broviac catheter was flushed with 100–200 units of heparin in 10 cc 0.9% NS.

Clinical Observations

The monkeys were observed daily for changes in weight, feeding, behavior, alertness, and neurologic function. The monkeys also were observed closely for signs of drug toxicity, including tremors, emesis, vomiting, diarrhea, seizures, and CNS depression [Sigma MSDS, CAS #366-18-7, 1994].

Laboratory Observations

Plasma samples were collected on days 0 and 7 of each experiment and were analyzed by Maryland Medical Pathology (Rockville, Md.) for serum iron and percent transferrin saturation. Due to the molecular complexity of iron chelators, direct assays for these drugs are not available.

Tissues were studied for gross and microscopic anatomic pathology by Dr. Michael Eckhaus and staff (Veterinary Resources Program, National Center for Research Resources, NIH, Bethesda, Md.).

Experimental Design

Pilot studies were done to determine the experimental dosage. The first pilot animal received 44 mg/kg/24 hours for 14 days and clinically showed no sign of toxicity and developed mild vasospasm (20%). The second pilot animal received up to 100 mg/kg/8 hours. This animal developed symptoms of toxicity (tremors, emesis, and diarrhea) and was sacrificed on the fourth day of drug delivery. These two pilot animals were then excluded from further data analysis.

Based on this data, an intermediate dosage of 70 mg/kg/day was used for all subsequent experimental animals (n=6).

Data Analysis

Image measurement was performed using a computerized image analysis program (Image 1.54, Rasband, NIH, Bethesda, Md.), as described previously [Pluta et al., J. Neurosurg. 77:740–748 (1992)]. The vessel was measured from the bifurcation of the ICA into the anterior cerebral artery and MCA to the point of the MCA trifurcation in the insula. This length, approximately 14 mm, corresponds to the region of MCA that was surgically stripped of arachnoid. Preoperative measurements in each animal were compared with measurements on postoperative day 7–10. Vasospasm was defined as >11% reduction of the area of the R MCA segment in the anteroposterior (AP) view, as described above. Mild vasospasm was defined as a reduction in the AP area of the defined segment of the MCA of 12–25%, moderate 26–50%, and severe >50% [Pluta et al., J. Neurosurg. 77:740–748 (1992)].

Statistical Measurements

Data are reported as means of measurements by three individuals ±SEM and compared using an unpaired chi-square test. Significance was accepted at $p<0.05$.

Results

The five control animals developed moderate vasospasm of the R MCA on POD 7–10. The mean AP area of the proximal portion of the MCA was 44.8%±4.6% ($p<0.0001$) of the baseline, preoperative area.

The six animals receiving 70 mg/kg/d had no spasm (FIG. 1). The mean AP area of the proximal portion of the MCA was 3.9%±4.3% ($p<0.0001$) of the baseline area. These animals received 70 mg/kg/day of DP for 14 days.

None of the control or treated animals experienced weight loss, changes in feeding habits, or alertness. Experimental animals #1, #2, and #4 developed mild tremors of the upper and lower extremities, and leg weakness. These symptoms resolved in animal #1 by day 4 and in animal #4 by day 6 but did not resolve in animal #2 by day 14. Animals #3, #5, and #6 had no toxic symptoms. Aside from the pilot animal receiving 100 mg/kg/8 hours, all animals had stable and equivalent blood pressures during preoperative and postoperative arteriography and experienced no blood pressure fluctuations throughout the 14-day treatment.

In the six treated animals, the mean serum iron concentration on day 0 was 109.0=18.0 ug/ml, and on day 7 was 2.0=2.0 ug/ml ($p<0.001$). The mean percent transferrin saturation on day 0 in the six experimental animals was 34.0=4.0%, and on day 7 was 1.2=2.0% ($p<0.0001$).

Gross pathology revealed no toxicity to the brain, liver, kidney, lymph nodes, spleen, intestine, gonads, or skeletal or cardiac muscle. Microscopic pathology revealed no toxicity to the brain (substantia nigra and cerebellar Purkinje cells were analyzed), lymph nodes, spleen, intestine, gonads, or skeletal or cardiac muscle.

Mild changes were observed in the liver. Hepato-cellular swelling was observed in animals #1, #3, #4, and #5. Hepatocellular degeneration was observed in animals #2 and #6 (Table 1).

Multifocal casts were observed in the collecting tubules of animals #2 and #5. No sign of nephrotoxicity was observed in animals #1, #3, #4, or #6 (Table 1).

TABLE 1

| Monkey | Fe D 0 µg/ml | Fe D 7 µg/ml | TransFe sat % Day 0 | TransFe sat % Day 7 | Toxicity Liver & Kidney |
|---|---|---|---|---|---|
| 102 | 105 | 5 | 40 | 2 | L+/K− |
| 103 |  | 1 |  | 0 | L++/K+ |
| I3254 | 101 | 1 | 32 | −1 | L+/K− |
| 10A | 96 | 1 | 31 | −2 | L+/K− |

TABLE 1-continued

| Monkey | Fe D 0 μg/ml | Fe D 7 μg/ml | TransFe sat % Day 0 | TransFe sat % Day 7 | Toxicity Liver & Kidney |
|---|---|---|---|---|---|
| N11 | 135 | 1 | 33 | −2 | L++/K− |
| 738PR |  | 1 |  | −4 | L+/K+ |
| Mean | 109 ± 18 | 2 ± 2 | 34 ± 4 | −1.2 ± 2 |  |
|  | $p < 0.001$ | $p < 0.0001$ |  |  |  |

Pathology
the liver- (L+) swelling of hepatocytes, (L++) degeneration, (L+++) lipidosis (#73, #105), regeneration (885N)
the kidneys- (K+) multifocal casts, (K++) glomerulonephritis (#73, #105), hemosiderin deposits (K−) no toxicity
No brain changes (substantia nigra, cerebellum- Purkinje cells)

The results of this study shows that a specific chelator of ferrous iron can prevent vasospasm in a primate model of SAH. In this primate model of SAH-related vasospasm, the reliability of producing spasm in untreated animals is 98% [Pluta et al., J. Neurosurg. 77:740–748 (1992)]. Six animals receiving 70 mg/kg/day of dipyridyl had no arteriographic vasospasm. The serum iron was markedly reduced in the drug-treated animals on day 7, as compared to day 0, confirming chelation of the plasma iron in the treated animals. The percent saturation for the endogenous chelator transferrin was decreased in treated animals, suggesting that dipyridyl strongly chelates iron. Furthermore, toxicity at the effective dose is mild.

What is claimed:

1. A method of preventing or treating cerebral vasospasm comprising:
   internally administering to a human who has suffered subarachnoid hemorrhage an effective amount of an iron chelator which preferentially chelates ferrous iron over ferric iron and which competes with nitric oxide binding to ferrous iron, thereby interfering with the nitric oxide sink effect,
   wherein said iron chelator is selected from the group consisting of 2,22'-dipyridyl and 1,10-phenanthroline.

2. The method of claim 1, wherein said iron chelator is internally administered through a route selected from the group consisting of a continuous IV, intravenous bolus, and oral.

3. The method of claim 1, wherein said iron chelator is internally administered to the human within 7 days of the subarachnoid hemorrhage.

4. The method of preventing or treating vasospasm of claim 1, wherein the said iron chelator further penetrates the blood-brain barrier and acts intracellularly.

5. The method of claim 2, wherein said route is intravenous bolus.

6. The method for the prevention or treatment of vasospasm of claim 1, wherein said iron chelator is 2,2' dipyridyl.

7. The method of claim 6, wherein said iron chelator is internally administered at a dose of 20–100 mg/kg/day.

8. A kit or labeled container for the prevention or treatment of cerebral vasospasm in a human who has suffered subarachnoid hemorrhage, comprising:
   a container;
   an effective amount of an iron chelator in said container which preferentially chelates ferrous iron over ferric iron and competes with nitric oxide binding to said ferrous iron thereby interfering with the nitric oxide sink effect; and
   instructions either secured to said container or associated with said kit which give directions on how to use said iron chelator for prevention or treatment of cerebral vasospasm in said human who has suffered subarachnoid hemorrhage, wherein said directions provide for internally administering said effective amount of said iron chelator to said human,
   wherein said iron chelator is selected from the group consisting of 2,2'-dipyridyl and 1,10-phenanthroline.

9. The kit or labeled container for the prevention or treatment of vasospasm of claim 8, wherein said iron chelator further penetrates the blood-brain barrier and acts intracellularly.

10. The kit or labeled container for the prevention or treatment of vasospasm of claim 8, wherein said iron chelator is 2,2' dipyridyl.

11. A pharmaceutical composition for the prevention or treatment of cerebral vasospasm comprising:
    an effective amount of an iron chelator which preferentially chelates ferrous iron over ferric iron and competes with nitric oxide binding to said ferrous iron thereby interfering with the nitric oxide sink effect and wherein said chelator is effective for preventing or treating cerebral vasospasm when administered internally to said human who has suffered subarachnoid hemorrhage; and
    a pharmaceutically acceptable carrier,
    wherein said iron chelator is selected from the group consisting of 2,2'-dipyridyl and 1,10-phenanthroline.

12. The pharmaceutical composition for the prevention or treatment of vasospasm of claim 11, wherein said iron chelator is 2,2' dipyridyl.

13. The pharmaceutical composition for the prevention or treatment of vasospasm of claim 11, wherein said iron chelator further penetrates the blood-brain barrier and acts intracellularly.

14. The pharmaceutical composition of claim 12, wherein said ferrous iron chelator is present in a concentration to allow the administration of an amount of 20–100 mg/kg/day.

15. The pharmaceutical composition of claim 12, wherein said ferrous iron chelator is present in concentration 0.5–50 mg/ml.

16. The pharmaceutical composition of claim 12, wherein said ferrous iron chelator is present in concentration 5–25 mg/ml.

* * * * *